United States Patent [19]
Stanko et al.

[11] Patent Number: 5,458,124
[45] Date of Patent: Oct. 17, 1995

[54] ELECTROCARDIOGRAPHIC SIGNAL MONITORING SYSTEM

[76] Inventors: Bruce E. Stanko, 4284 Lampl Rd., Allison Park, Pa. 15101; David G. Ellertson, 7105 Hillcrest Dr., Modesto, Calif. 95356

[21] Appl. No.: 193,277

[22] Filed: Feb. 8, 1994

[51] Int. Cl.[6] ............................................. A61B 5/0408
[52] U.S. Cl. ......................... 128/696; 128/903; 128/640
[58] Field of Search ................................. 128/639, 640, 128/641, 696, 903

[56] References Cited

U.S. PATENT DOCUMENTS

| | | |
|---|---|---|
| 3,253,588 | 5/1966 | Vuilleumier et al. |
| 3,832,994 | 9/1974 | Bicher et al. |
| 3,943,918 | 3/1976 | Lewis. |
| 3,972,320 | 8/1976 | Kalman. |
| 4,494,553 | 1/1985 | Sciarra et al. |
| 4,819,860 | 4/1989 | Hargrove et al. |
| 4,889,131 | 12/1989 | Salem et al. |
| 4,981,141 | 1/1991 | Segalowitz. |
| 5,024,227 | 6/1991 | Schmid .................... 128/640 |
| 5,025,808 | 6/1991 | Hafner. |
| 5,036,869 | 8/1991 | Inahara. |

*Primary Examiner*—William E. Kamm
*Assistant Examiner*—Scott M. Getzow
*Attorney, Agent, or Firm*—Reed Smith Shaw & McClay

[57] ABSTRACT

A wireless transmitter module for use in a system for monitoring at least one physiological condition of a subject. The transmitter module includes a housing and an electrode patch preferably having three closely spaced electrodes provided on a first surface thereof. The first surface of the patch is coated with a non-allergenic adhesive in regions surrounding the electrodes, whereby the patch is securable to the subject by the adhesive to permit sensing of a physiological signal of the subject by the electrodes. The transmitter module further includes circuitry internal of the housing for detecting a physiological signal sensed by the electrodes and for transmitting a signal corresponding to the physiological signal to a receiving unit. Additionally, the module has snaps for detachably connecting the electrode patch to the exterior of the housing, the snaps being operable to effect electrical communication of the electrodes with the circuitry when the electrode patch is connected to the housing, whereby the entirety of the transmitter module is supported by the electrode patch when the electrode patch is connected to the housing and the first surface is adhered to the subject.

27 Claims, 6 Drawing Sheets

ELECTROCARDIOGRAPHIC SIGNAL MONITORING SYSTEM

FIELD OF THE INVENTION

The present invention relates in general to physiological monitoring equipment and, more particularly, to a wireless electrocardiographic (ECG) signal sensing and transmitting unit, wherein the unit employs disposable electrode patches in the form of sensor carrying substrates of compact configuration. The invention further contemplates a portable and wireless ECG monitoring system including the ECG sensing and transmitting unit and a receiver unit for receiving signals transmitted by the ECG sensing and monitoring unit, whereby the receiving unit has the capability to display real-time information corresponding to a patient's ECG signals.

BACKGROUND OF THE INVENTION

It is well known to continuously monitor one or more physiological conditions of certain subjects of clinical studies, athlete s or medical patients. The monitored conditions may include, but are not limited to, ECG activity, pulse rate, respiration rate, body temperature and blood pressure.

Today's medical patient monitoring systems, for example, are highly sophisticated telemetry systems particularly at the central receiving or monitoring stations. Indeed, medical technology has progressed to the point where central monitoring stations now consist of mainframes with interchangeable receiver modules that can be updated to avoid obsolescence. These modules receive and record such individual physiological parameters as ECG signals, arterial and pulmonary arterial characteristics, central venous pressure dynamics and peripheral pulse oximetric data.

While recent research and development has focused on state-of-the-art mainframe and module improvements, relatively little research has been directed toward improving input systems (transmitters) located at the patient-system interface. These transmitters are used to detect physiological parameters (most commonly ECG signals) and send these signals via radio frequency to the central receiving stations. It is not uncommon to have thirty (30) or more receiving monitors in operation simultaneously in an average sized hospital.

Conventional single channel ECG telemetry transmitter units normally consist of three major components:

1. Three (3) independent electrodes or sensors
2. Three (3) lead cables
3. Transmitter and battery pack Hospitalized patients that require ECG telemetry monitoring thus must endure the encumbrances of elongated cables (usually three to five feet in length) that independently connect generally three ECG sensor electrodes to a transmitter and battery pack housing. Typical electrode patches are approximately two inches in diameter, usually circular, and adhere to the skin firmly with biologically compatible adhesive. They are conventionally placed just below the left and right shoulder and the left side of the upper abdomen at an approximate distance of between about 15 to 20 inches for a typical adult patient. The cables are commonly run through the patient's shirt sleeve or beneath the bed clothing. The transmitter and battery pack housings are formed as a plastic case measuring approximately 4×7× 1.5 inches and are placed in paper pouches that are attached to the patient's clothing with a safety pin or the like. With a transmitter unit so constructed and arranged, the patient is burdened by the bulky transmitter housing and the lead cables that are apt to be caught on bed rails, lavatory equipment, food trays, IV poles and other objects regularly encountered by the patient. Additionally, the cables are prone to entangle and dislodge from the patient, thereby interrupting signal transmission.

Further, when a patient is undergoing an operation, a mainframe monitor is permanently stationed in the operating room for enabling the anesthesiologist to monitor vital signs such as heart rate and ECG signals. Upon completion of the operation, the patient is placed upon a transportable bed and moved to a recovery area. It is during this transportation that the sensor lead cable connections of conventional systems often become dislodged or entangle with other wires or intravenous (IV) tubing. Additionally, a rather large and heavy monitor must accompany the patient, thereby compounding the difficulties attendant to this delicate postoperative patient transport period.

Examples of ECG monitoring systems which describe sophisticated developments in mainframe technology can be found in U.S. Pat. Nos. 3,832,994, 4,981,141, 5,025,808 and 5,036,869. These patents, however, provide little disclosure as to the construction or operation of their patient-carried ECG sensors. Additionally, each recite conventional practice as to sensor placement on the patient's body, i.e., widely separated across the patient's torso or, in the case of U.S. Pat. No. 5,025,808, on the patient's arms and legs.

U.S. Pat. Nos. 3,972,320, 4,494,553, 4,889,131 and 4,819,860 represent various endeavors in physiological monitoring system apparatus particularly directed to the remote sensors carried by the patient. Of these, U.S. Pat. No. 3,972,330 and 4,819,860 teach of wrist-carried sensors which transmit to a central receiving station data signals corresponding to detected physiological conditions; whereas, U.S. Pat. No. 4,494,553 and 4,889,131 each describe belt-like sensor equipment that is worn about a user's torso.

U.S. Pat. No. 3,253,588 describes user-carried physiological sensors of complex construction and operation. The sensors include not only means for detecting a particular physiological condition, but also means for receiving an interrogation signal from a remote station and means responsive to the interrogation signal for transmitting to the remote station a signal corresponding to the detected physiological condition.

U.S. Pat. No. 3,943,918 discloses a disposable physiological telemetric sensor including microcircuitry, wiring and multiple electrodes and batteries, all at which are discarded after a single use of the sensor. As will be appreciated, the waste attendant to disposal of the sensors and the many internal electrical components thereof after a single application renders usage of Such sensors somewhat impractical and economically unattractive from the perspective of large-scale users of such equipment, e.g., health care providers such as hospitals, clinics and nursing homes.

An advantage exists, therefore, for a telemetric physiological condition (particularly an ECG signal) sensing and transmitting unit that is compact, unobtrusive to the wearer, uncomplicated in design, and offers comparatively inexpensive and reliable long-term service. A further advantage exists for a system incorporating such a sensing and transmitting unit and a lightweight and completely portable receiver unit capable of displaying in real-time visual information corresponding to the patient's physiological signals,

SUMMARY OF THE INVENTION

According to the present invention, there is provided a miniature ECG signal detecting and transmitting module that is typically worn by a patient during hospital stays. The module comprises a rugged, non-conductive plastic housing containing the essential ECG signal detection and radio frequency transmission circuitry, as well as a DC power source. Additionally, the module includes an electrode patch externally and detachably connectable to the housing. The patch receives the patient's ECG signals and, when attached to the housing, is electronically connected to the ECG signal detection circuitry.

In accordance with the presently preferred embodiment, the detachable electrode patch supports three ECG electrodes in close array (generally less than about two and one-quarter inches apart) in either a substantially triangular or substantially linear arrangement. In operation, the electrode patch is attached to the housing via conventional connector structure. The patch, and thus the module housing to which it is attached, are secured to the patient's chest wall with a suitable bio-compatible adhesive provided on the exposed surface of the patch. Once properly placed, the power source in the module housing can be activated whereby monitoring of the patient's ECG activity may proceed.

Due to the compact size of the module in addition to the absence of cumbersome external electrode wiring, patient mobility, comfort and safety, as well as ECG signal reading accuracy, are enhanced, while opportunities for inadvertent dislodgment of the electrodes are minimized. Further, the absence of the electrode wires also eliminates bothersome signal artifacts associated with such wires.

The detecting and transmitting module, hereinafter referred to as the "transmitter module" is thus a self contained battery operated and wireless device for transmitting ECG signals to a receiving unit. The transmitter module has the unique ability to detect signals via the triple-electrode patch which has closely spaced electrode pickup pads, Unlike other existing designs, the transmitter module is attached directly to the patient by the adhesive patch placed on the upper chest area. The electrode patch is preferably secured to the module housing by a series of quick-disconnect snaps thus enabling simplified and inexpensive electrode replacement while eliminating unwieldy electrode cables.

The transmitter module is preferably activated by simply installing the battery and remains active until the battery is removed. In accordance with the preferred embodiment, there are no external user controls on the instrument. All controls are internally located and are intended for adjustment by authorized technical personnel only. The module also has the unique feature of switch selectable channel settings. This obviates the need for special circuit components and technical equipment to tune the transmitter to a desired channel.

Along with the basic ECG signal, the module desirably transmits appropriate signals to alert the receiver operator of conditions such as electrode connection problems and low battery voltage.

Further, because no single electrode patch configuration will work suitably for all patients, an optional patch configuration is available to allow connection of a branched electrode. This permits optimum location of the branched electrode to obtain a usable signal.

Additionally, the present invention contemplates an ECG monitoring system incorporating the aforementioned ECG transmitter module and a small, lightweight, portable and wireless receiver module for displaying real-time information corresponding to the patient's ECG signals. According to the presently preferred embodiment, the receiver module resembles a lap-top computer with an LCD screen having dimensions of approximately five by seven inches. Most preferably, the receiver module and the transmitter module are a kit, whereby the transmitter module is stored interiorly of the receiver module when not in use. A particular advantage of this miniaturized, entirely wireless monitoring system is realized when transporting patients from the operating room to a postoperative recovery area.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
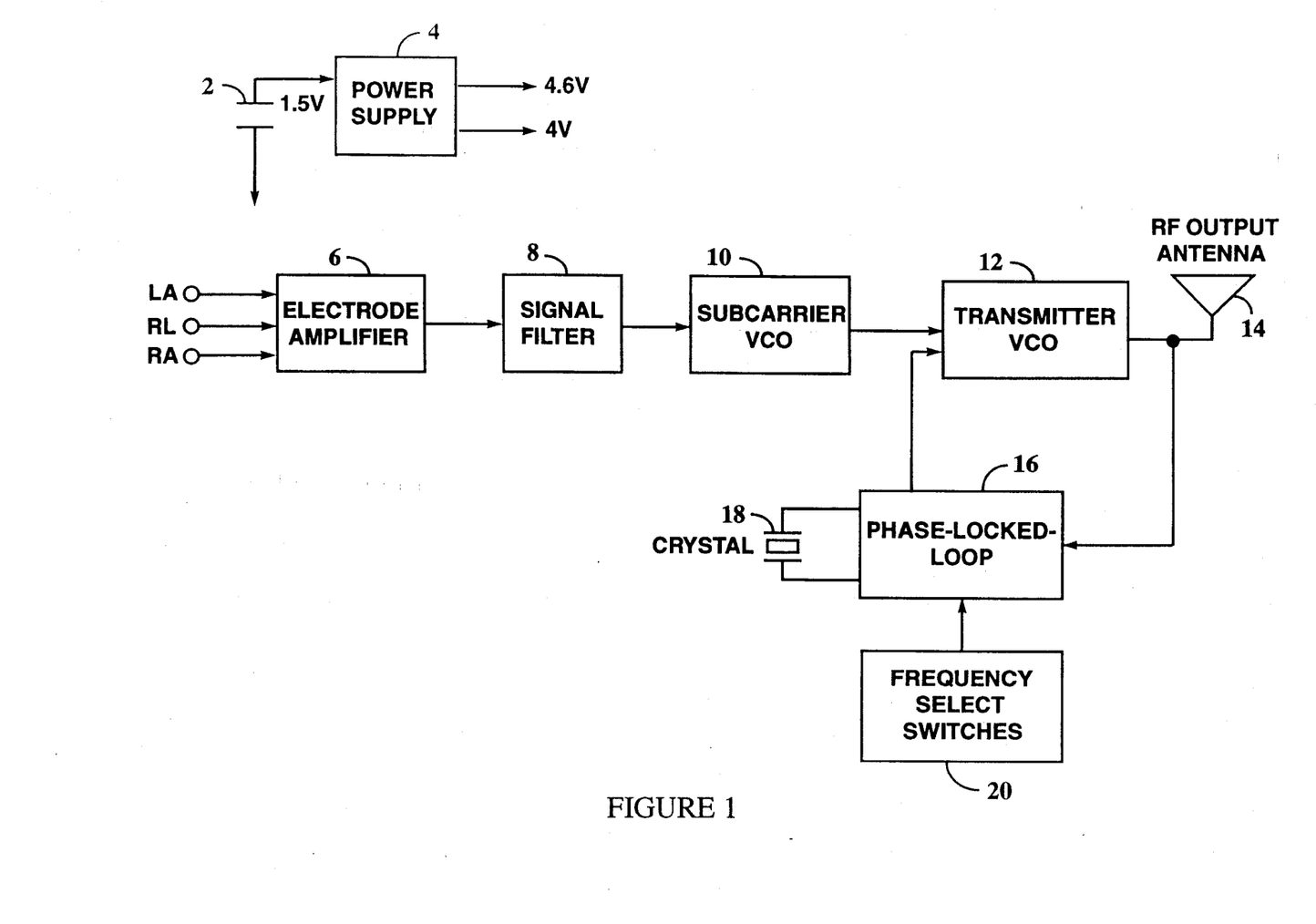
FIG. 1 is a schematic diagram broadly representing the general circuitry operation of the transmitter module of the present invention.

With reference to FIG. 1, there is illustrated the general operational scheme of the ECG signal detecting and transmitting circuitry employed and housed in the transmitter module (described hereinbelow) of the present invention. Although the circuitry may be appropriately modified so as to function with any suitable miniature DC power source, e.g., a 1.5 V to a 9 V alkaline, nickel cadmium or lithium battery, it is presently preferred that the entire circuitry derive power from a conventional 1.5 V "AA" cell alkaline battery 2. The power supply circuit 4 converts the 1.5 V of the battery 2 to a precisely regulated +4.0 V and +4.6 V source as needed by the transmitter circuitry. More particularly, the power supply circuit 4 includes a step-up switching regulator which steps up the battery voltage to +4.6 V and an inductor that stores energy at the 1.5 V level and transforms it to an equivalent energy level at 4.6 V. Since the actual regulator circuit produces a voltage of 4.6 V, the 4.0 V output may be produced by passing the 4.6 V through a suitable diode or the like to drop the voltage by 0.6 V, thus producing a nominal 4.0 V to be used solely by the transmitter voltage controlled oscillator (VCO) to be described hereinafter.

The regulator also incorporates a low battery detector that produces a trip signal at a battery voltage of about 1.0 V to disable the transmitter VCO whereby the module will not transmit on the selected channel in the event of a low battery condition.

An electrode amplifier 6 receives electrocardiographic signals via three electrodes LA, RL and RA carried in closely spaced array by a single electrode patch which forms a component of the novel transmitter module of the instant invention. The electrode amplifier 6 integrates the detected electrocardiographic signals into a single signal and amplifies same to a first power level.

A signal filter 8 receives the amplified electrocardiographic signal from the electrode amplifier 6, further amplifies it in conjunction with bandpass filtering to limit the transmitted signal to frequencies in the range of about 0.08 to about 80 Hz. This particular range of transmission frequency is desirable for rendering the transmitter module compatible with existing mainframe receiving units and also for minimizing unwanted signal noise.

A subcarrier VCO 10 receives the amplified and filtered signal from the signal filter 8. The subcarrier VCO is an oscillator which produces a nominal 1000 Hz signal. This signal is frequency modulated in proportion to the actual electrode input signal. Hence, if the input signal moves in a positive direction, the subcarrier VCO output frequency increases. Should the input signal shift to a negative direction, the subcarrier VCO output frequency decreases.

The transmitter VCO 12 is the final radio frequency (RF) output device to the RF output antenna 14. The frequency modulated signal from the subcarrier VCO 10 is used to further frequency-modulate the final RF carrier signal of the transmitter VCO 12. Because of its double frequency modulation scheme, this type of transmission is known as FM—FM modulation and provides the maximum protection from signal interference.

The transmitter VCO 12 has two inputs, one for signal (subcarrier VCO 10) modulation and one for RF carrier modulation. The actual RF carrier modulation is what sets the transmitter VCO to the proper frequency for a given channel. This channel selection is controlled by the phase-locked-loop 16. The phase-locked-loop 16 is an ultra-stable crystal controlled circuit which compares the RF output frequency to the reference frequency controlled by crystal 18 and adjusts the transmitter VCO 12 accordingly to cause the two to match. By digitally varying the phase-locked-loop 16 internal reference frequency, the transmitter can be easily set for any standard channel in the range of 430–470 MHz provided the proper transmitter VCO 12 is used. The variation of reference frequency is accomplished by setting a series of frequency switches 20 on the transmitter board. It will be further appreciated that through selective adjustment of the circuitry components thus far described the transmitter module can be programmed to transmit either UHF or VHF signals. Likewise, the module may broadcast at frequencies compatible with virtually all presently available stationary or transportable receiver units, as well the hand-portable receiver module of the present invention, which is described in greater detail later herein.

As mentioned above, the signal from the transmitter VCO 12 is fed to a RF output antenna 14 which emits the signal to be received by the receiver unit. According to the present invention, the RF output antenna is an integral miniature antenna which obviates the need for lengthy external lead cables to transmit the signal. And, although not illustrated herein because it does not constitute a central feature of the instant invention nor is necessary for understanding thereof, the circuitry described hereinabove also preferably includes appropriate components to transmit signals to alert medical personnel at the receiving unit of problematic conditions such as misconnected electrode(s) or low battery voltage.

Turning to FIGS. 2–5, there is depicted a presently preferred embodiment of a transmitter module 22 constructed according to the present invention. The module 22 includes a housing 24 fabricated from non-conductive, impact-resistant plastic and formed into first and second body portions 26 and 28. Body portion 26 is the main body portion and internally houses the ECG signal detecting and transmitting circuitry described above. Body portion 28 is a detachable cap member that may be releasably engageable with body portion 26 via a friction fit, releasable latch members, or other suitable means.

Figure 2:
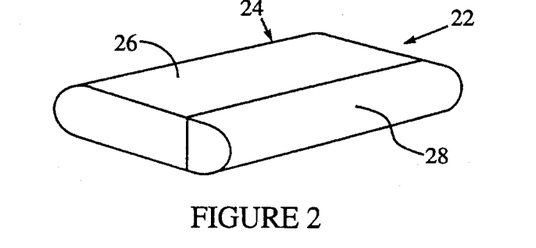
FIG. 2 is a perspective view of a preferred embodiment of the transmitter module constructed according to the present invention.
Figure 3:
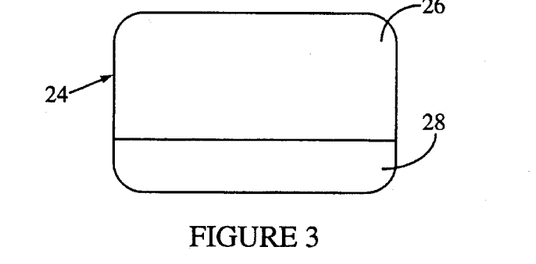
FIG. 3 is a top view of the module illustrated in FIG. 2.

For simplicity, it is preferred that the transmitter module 22 be activated simply by removing the cap member 28, installing the battery 2, and rejoining the cap member to the main body portion. Hence, the module remains continuously operational as long as the battery possesses sufficient voltage (typically several days) or until the battery is removed. Although the module 22 may be provided with external circuitry adjustment controls, it is preferred that all such controls (e.g., the frequency select switches 20) be internally located, whereby they may be precisely adjusted by authorized personnel and are not subject to inadvertent misadjustment or tampering by the wearer of the module.

Figure 4:
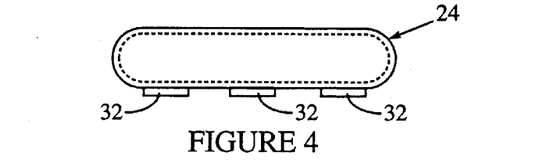
FIG. 4 is an end view of the module illustrated in FIG. 2.
Figure 5:
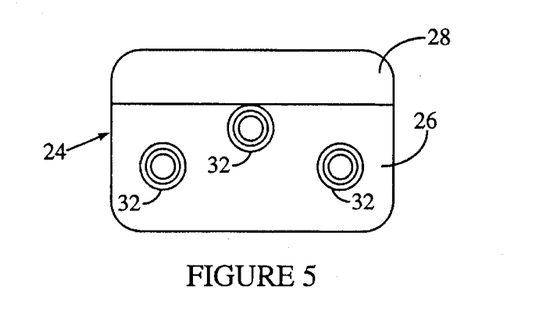
FIG. 5 is a bottom view of the module illustrated in FIG. 2 with the electrode patch thereof omitted for clarity.
Figure 6:
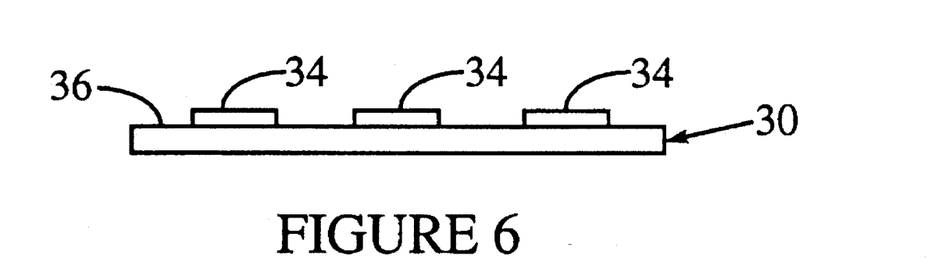
FIG. 6 is an edge view of an electrode patch which forms a component of the transmitter module of the present invention.
Figure 7:
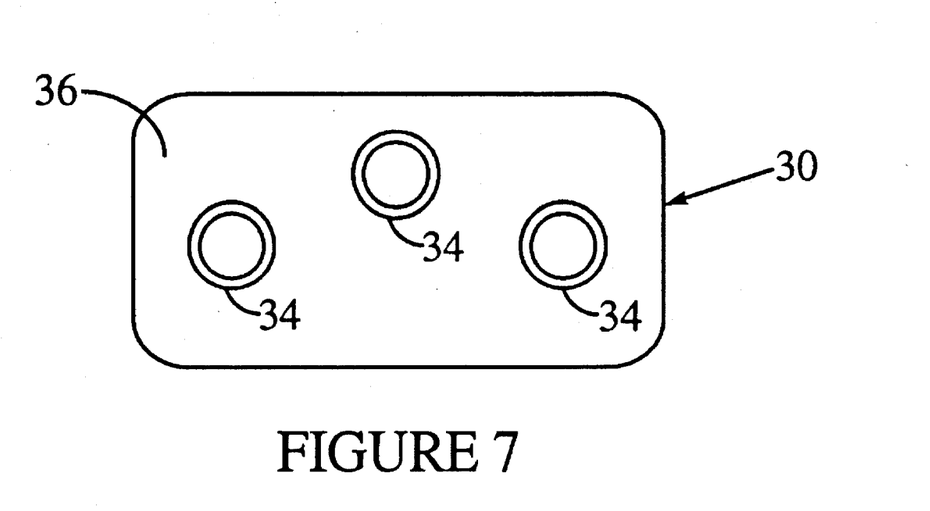
FIG. 7 is a rear surface view of the electrode patch of FIG. 6.

According to the present invention, the transmitter module 22 also comprises a novel detachable electrode patch 30 that is described later herein with reference to FIGS. 6–9. In this connection, as is illustrated in FIGS. 4 and 5, the transmitter module 22 further includes means externally of the housing 24, but in electrical communication with the internal detecting and transmitting circuitry thereof, for enabling the electrode patch 30 to be detachably connected to the module housing. Pursuant to the presently preferred embodiment, the means for enabling detachable connection of the electrode patch 30 to the housing 24 comprise conventional metallic snap connectors. These snap connectors may assume the form of conventional circular "female" metallic connectors 32 adapted to matingly receive corresponding "male" metallic connectors 34 provided at the rear surface 36 (FIGS. 6 and 7) of electrode patch 30. Alternatively, the electrode patch may carry the female connectors and the module housing the male connectors. Other suitable connection means will be appreciated by those skilled in the art. For example, the module housing body portion 26 may be formed with projecting parallel rails which may slidably receive corresponding structure provided on the rear surface of the electrode patch, with both the electrode patch and the housing having correspondingly arranged metallic contacts. Accordingly, when the electrode patch is sufficiently engaged with the rails and properly positioned relative to the housing, the metallic contacts of the electrode patch and the housing body portion will be brought into electrical communication.

Figure 8:
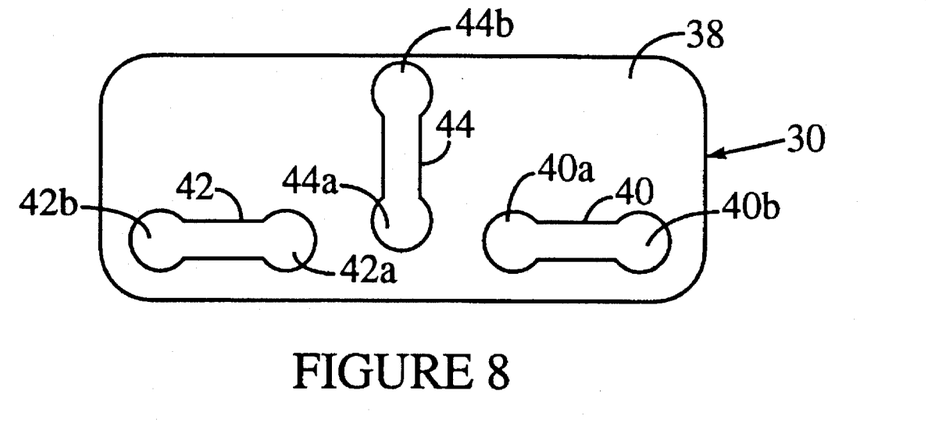
FIG. 8 is a front surface view of the electrode patch of FIGS. 6 and 7 illustrating a first preferred electrode arrangement thereof.

FIG. 8 reveals a first preferred arrangement of the electrode array that is formed on the front surface 38 of electrode patch. The electrode array consists of three electrodes 40, 42 and 44 corresponding respectively to the primary electrodes RA (right arm) and LA (left arm) and the secondary electrode RL (right leg) shown in FIG. 1. The electrodes 40, 42 and 44 are formed of conventional non-allergenic electrically conductive material such as, for example, a silver-silver chloride composition and are in electrical communication with the connection means 34 at the rear surface 36 of patch 30. Moreover, the exposed surfaces of the electrodes are coated with non-allergenic, electronically conductive gel material such as silver chloride jelly, while the balance of front surface 38 is coated with a bio-compatible non-allergenic adhesive.

Unlike conventional electrodes, electrodes 40, 42 and 44 are preferably non-circular in shape. Instead, the preferred configuration is generally elongated with somewhat enlarged opposite ends 40a, 40b, 42a, 42b and 44a, 44b. The enlarged electrode ends 40b, 42b and 44b, are arranged in a closely spaced generally triangular array and are situated on surface 38 in general mirror-image spatial correspondence with connectors 34 on opposing surface 36. It is also contemplated that electrode ends 40b, 42b and 44b may be placed in generally linear array. Regardless of the selected geometry of the electrode placement on patch 30, the maximum preferred distance between the furthest spaced of the electrode ends, i.e., 40b and 42b, is generally no more than about two and one-quarter inches center-to-center. In this regard, developmental trials of the instant invention have shown successful ECG signal detection and transmission with maximum electrode spacing as little as one and five-sixteenth inches. Further, the geometry or pattern of the electrode placement in the patch 30 exemplified in FIG. 8 has realized reliable results in a substantial majority of the subjects with whom it has been tested.

Figure 9:
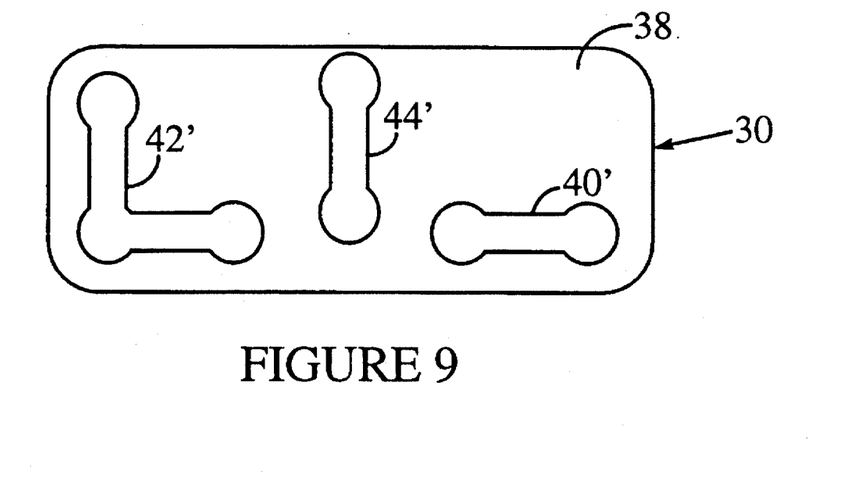
FIG. 9 is a view similar to FIG. 8 depicting a further preferred electrode arrangement of the electrode patch.

The electrode patch 30 shown in FIG. 9 represents a basically similar electrode array to that represented in FIG. 8. Indeed, electrodes 40' and 44' of FIG. 9 are configured and arranged essentially identically to their counterparts 40 and 44 of FIG. 8. Electrode 42', however, differs from electrode 42 in that in addition to its first elongated branch which extends essentially parallel to electrode 40', it further comprises a contiguous second elongated branch extending generally transverse to the first branch (and generally parallel to electrode 44'). The electrode patch 30 of FIG. 9 thus affords an alternative and optional electrode configuration which has been effectively employed when an electrode array like that depicted in FIG. 8 has not provided adequate ECG signal detection for a particular patient. As with the electrode patch of FIG. 8, the electrodes 40', 42' and 44' are coated with non-allergenic electrically conductive gel with the remainder of front surface 38 bearing a suitable non-allergenic, bio-compatible adhesive.

To operate the transmitter module 22, a medical doctor, nurse or technician installs a battery in the transmitter module housing 24, selects an electrode patch 30 having an electrode array configuration appropriate for the subject or patient to be monitored and connects the patch to the housing, such as by the mating snap connectors 32 and 34. Thereafter, the medical professional removes an unillustrated protective cover from the front face 38 of the electrode patch, thereby exposing the non-allergenic conductive gel and adhesive respectively coating the electrodes and their surrounding regions. Then, while monitoring signal strength on a nearby receiver unit, the medical professional moves the module over the subject's upper left chest region until a clear and powerful ECG signal is displayed on the receiver unit, whereupon the unit is then gently but firmly pressed into position on the subject's chest at the desired location. As such, the entirety of the transmitter module 22 is supported on the patient by the electrode patch by virtue of the adhesive on front surface 38.

Included among the many advantages of the transmitter module construction of the present invention are that:

(1) it is completely wireless, thereby eliminating the unwieldiness, obtrusiveness and signal distortion associated with lengthy electrode lead cables;

(2) it is compact and lightweight and enables accurate, real-time ECG signal monitoring using a single electrode patch having a triple electrode array far more closely spaced than can be achieved through individually placed electrodes of the type heretofore known in the art; and (3) it is highly economical to use in that the module housing and its internal ECG signal detecting and receiving circuitry may be repeatedly reused, whereas only the relatively simple and inexpensive electrode patch and, perhaps, the battery require replacement after each use.

Figure 10:
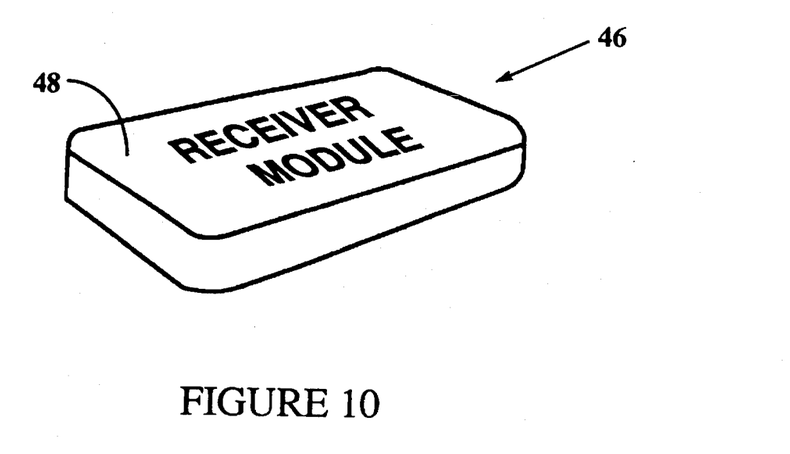
FIG. 10 is a perspective view, in a closed condition, of a presently preferred embodiment of a receiver module constructed to operate in conjunction with the transmitter module of the present invention.
Figure 11:
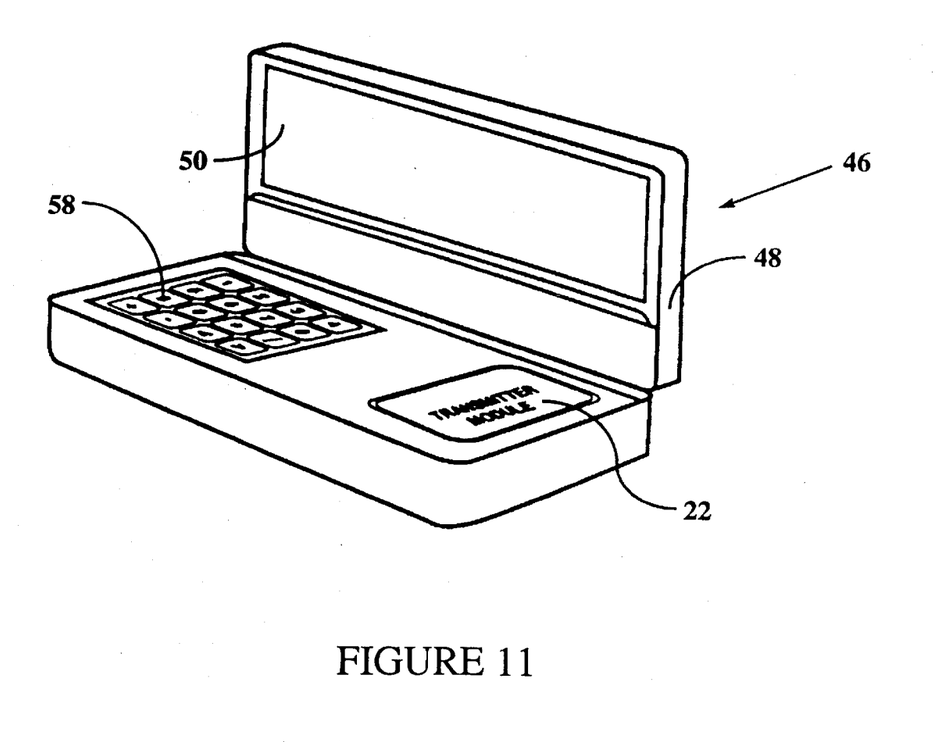
FIG. 11 is a perspective view of the receiver module of FIG. 10 in open condition.
Figure 12:
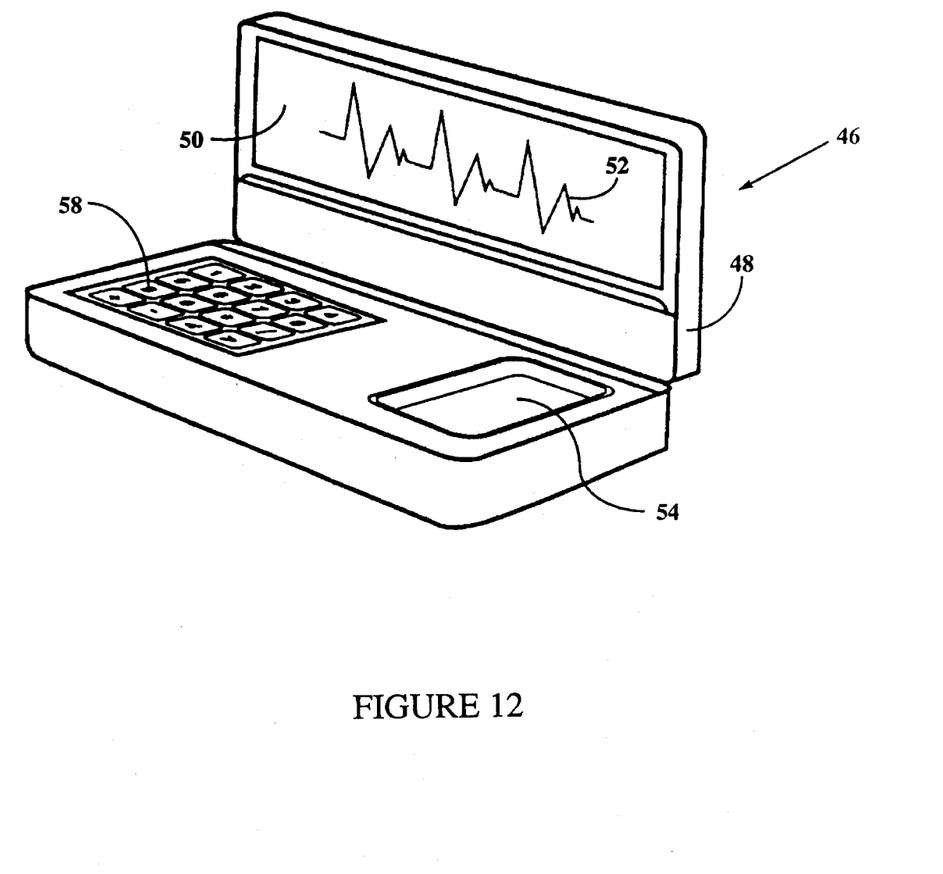
FIG. 12 is a view similar to FIG. 11 with the receiver module shown in operation.

Further encompassed within the scope of the present invention is an ECG signal monitoring system utilizing the above-described transmitter module 22 in combination with a lightweight and hand-portable receiver module. A receiver module contemplated by the invention is revealed in FIGS. 10–12 and is designated by reference numeral 46. In accordance with the presently preferred embodiment, receiver module 46 resembles a lap-top computer, its hinged cover 48 being shown closed in FIG. 10 and open in FIGS. 11 and 12. Cover 48 incorporates an integral LCD screen 50 having dimensions of approximately five by seven inches for displaying, inter alia, a real-time graphic representation (reference numeral 52) of a patient's ECG signal. Most desirably, the receiver module 46 and the transmitter module 22 are a kit as is depicted in FIG. 11. That is to say, when the monitoring system is not in use, the transmitter module is stored in a compartment 54 in the base portion 56 of the receiver module 46 (FIG. 12). As will be appreciated, the base portion 56 of the receiver module 46 also includes the requisite ECG signal receiving and processing circuitry (not described in detail herein) that is necessary to enable an ECG signal 52 to be displayed on screen 50. Moreover, the base portion 56 includes an alphanumeric keyboard 58 to enable the medical professional to modify certain parameters of the signal receiving and processing circuitry as necessary to attune the receiver module with the transmitter module.

The miniaturized entirely wireless ECG signal monitoring system according to the present invention finds beneficial usage in virtually any conceivable environment or situation where precise ECG monitoring is required. For example, its utility will be readily appreciated when employed during transport of a surgery patient to a postoperative recovery area.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A wireless transmitter module for use in monitoring at least one physiological condition of a subject, said transmitter module comprising:

a housing having an interior and an exterior;

an electrode patch including at least one electrode provided on a first surface thereof, said first surface being coated with a biologically compatible adhesive in regions surrounding said at least one electrode, said electrode patch being securable to said subject by said adhesive to permit sensing of a physiological signal of said subject by said at least one electrode;

circuitry means contained within said interior for detecting a physiological signal sensed by said at least one electrode and for transmitting a signal corresponding to said physiological signal to a receiving unit; and means for detachably connecting said electrode patch to said exterior of said housing, said means for detachably connecting being operable to effect electrical communication of said at least one electrode with said circuitry means when said electrode patch is connected to said housing, whereby the entirety of said transmitter module is supported by said electrode patch when said electrode patch is connected to said housing and said first surface is adhered to said subject.

2. The transmitter module of claim 1 where said electrode patch includes three electrodes provided on said first surface.

3. The transmitter module of claim 2 wherein maximum spacing between said electrodes is no greater than about two and one-quarter inches.

4. The transmitter module of claim 3 wherein said electrodes are arranged in a generally triangular array.

5. The transmitter module of claim 2 wherein said electrodes are elongated in configuration.

6. The transmitter module of claim 5 wherein at least one of said electrodes comprises at plurality of elongated branches.

7. The transmitter module of claim 1 wherein said means for detachably connecting comprise cooperating snap connectors carried by the exterior of said housing and by a second surface of said electrode patch facing opposite said first surface thereof.

8. The transmitter module of claim 1 wherein said physiological signal sensed by said at least one electrode is an electrocardiographic signal.

9. The transmitter module of claim 1 wherein said signal corresponding to said physiological signal is a radio frequency signal.

10. A wireless system for monitoring at least one physiological condition of a subject, said system comprising:

a hand-portable receiver module; and a transmitter module comprising:

a housing having an interior and an exterior;

an electrode patch including at least one electrode provided on a first surface thereof, said first surface being coated with a biologically compatible adhesive in regions surrounding said at least one electrode, said electrode patch being securable to said subject by said adhesive to permit sensing of a physiological signal of said subject by said at least one electrode;

circuitry means contained within said interior for detecting a physiological signal sensed by said at least one electrode and for transmitting a signal corresponding to said physiological signal to said receiver module; and means for detachably connecting said electrode patch to said exterior of said housing, said means for detachably connecting being operable to effect electrical communication of said at least one electrode with said circuitry means when said electrode patch is connected to said housing, whereby the entirety of said transmitter module is supported by said electrode patch when said electrode patch is connected to said housing and said first surface is adhered to said subject.

11. The system of claim 10 where said electrode patch includes three electrodes provided on said first surface.

12. The system of claim 11 wherein maximum spacing between said electrodes is no greater than about two and one-quarter inches.

13. The system of claim 12 wherein said electrodes are arranged in a generally triangular array.

14. The system of claim 11 wherein said electrodes are elongated in configuration.

15. The system of claim 14 wherein at least one of said electrodes comprises at plurality of elongated branches.

16. The system of claim 10 wherein said means for detachably connecting comprise cooperating snap connectors carried by the exterior of said housing and by a second surface of said electrode patch facing opposite said first surface thereof.

17. The system of claim 10 wherein said physiological signal sensed by said at least one electrode is an electrocardiographic signal.

18. The system of claim 10 wherein said signal corresponding to said physiological signal is a radio frequency signal.

19. The system of claim 10 wherein said receiver module includes means for receiving said signal corresponding to said physiological signal and screen means for graphically representing said physiological signal.

20. The system of claim 19 wherein said graphic representation is a real-time representation of said physiological signal.

21. The system of claim 10 wherein said receiver module includes means for storing said transmitter module when said system is not in use.

22. An electrode patch for use in sensing a physiological signal of a subject, said electrode patch comprising:

a first surface;

three electrodes provided on said first surface, said first surface being coated with a biologically compatible adhesive in regions surrounding said electrodes, said electrode patch being securable to said subject by said adhesive to permit sensing of said physiological signal of said subject by said electrodes;

a second surface facing opposite said first surface; and connection means carried by said second surface for enabling detachable connection of said electrode patch to the exterior of a physiological signal transmitter module housing and for electrically communicating said electrodes with signal detecting and transmitting circuitry situated internally of said housing, whereby the entirety of said housing is supported by said electrode patch when said electrode patch is connected to said housing and said first surface is adhered to said subject.

23. The electrode patch of claim 22 wherein maximum spacing between said electrodes is no greater than about two and one-quarter inches.

24. The electrode patch of claim 23 wherein said electrodes are arranged in a generally triangular array.

25. The electrode patch of claim 22 wherein said electrodes are elongated in configuration.

26. The electrode patch of claim 25 wherein at least one of said electrodes comprises at plurality of elongated branches.

27. The electrode patch of claim 22 wherein said connection means comprise snap connectors.

* * * * *